(12) United States Patent
Quan

(10) Patent No.: US 12,070,351 B2
(45) Date of Patent: *Aug. 27, 2024

(54) IMAGING SYSTEMS AND METHODS THEREOF

(71) Applicant: SHANGHAI UNITED IMAGING HEALTHCARE CO., LTD., Shanghai (CN)

(72) Inventor: Guotao Quan, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/161,866

(22) Filed: Jan. 30, 2023

(65) Prior Publication Data

US 2023/0165556 A1  Jun. 1, 2023

Related U.S. Application Data

(63) Continuation of application No. 16/950,889, filed on Nov. 17, 2020, now Pat. No. 11,564,653, which is a
(Continued)

(51) Int. Cl.
*A61B 6/00* (2024.01)
*A61B 6/03* (2006.01)
(Continued)

(52) U.S. Cl.
CPC ............ *A61B 6/545* (2013.01); *G06T 7/70* (2017.01); *G16H 30/20* (2018.01); *G16H 40/63* (2018.01);
(Continued)

(58) Field of Classification Search
CPC ........ G16H 30/20; G16H 40/63; G16H 50/20; G16H 50/50; A61B 6/032; A61B 6/037;
(Continued)

(56) References Cited

U.S. PATENT DOCUMENTS 10,006,758 B2   6/2018  Yan
10,331,850 B2   6/2019  Singh et al.
(Continued)

FOREIGN PATENT DOCUMENTS

CN       1742679 A    3/2006
CN     102096804 A    6/2011
(Continued)

OTHER PUBLICATIONS

International Search Report for PCT/CN2017/088375 mailed on Feb. 26, 2018, 4 pages.
(Continued)

*Primary Examiner* — Katrina R Fujita
(74) *Attorney, Agent, or Firm* — METIS IP LLC

(57) ABSTRACT

The present disclosure relates to a method, system and non-transitory computer readable medium. In some embodiments, the method includes: acquiring image data of a target subject positioned on a scanning table; determining, by a processor, first position information of the target subject based on the image data; determining, by the processor, second position information related to a scan region of the target subject based on the image data; and scanning, using an imaging device, the target subject based on the first position information and the second position information.

20 Claims, 10 Drawing Sheets

Related U.S. Application Data continuation of application No. 15/709,703, filed on Sep. 20, 2017, now Pat. No. 10,856,832, which is a continuation of application No. PCT/CN2017/088375, filed on Jun. 15, 2017.

(51) Int. Cl.
| | | |
|---|---|---|
| *A61B 6/04* | (2006.01) | |
| *G06T 7/70* | (2017.01) | |
| *G16H 30/20* | (2018.01) | |
| *G16H 40/63* | (2018.01) | |
| *G16H 50/20* | (2018.01) | |
| *G16H 50/50* | (2018.01) | |

(52) U.S. Cl.
CPC ............. *G16H 50/20* (2018.01); *G16H 50/50* (2018.01); *A61B 6/032* (2013.01); *A61B 6/037* (2013.01); *A61B 6/0407* (2013.01); *A61B 6/5205* (2013.01); *A61B 6/563* (2013.01); *G06T 2207/10081* (2013.01); *G06T 2207/20081* (2013.01); *G06T 2207/20084* (2013.01)

(58) Field of Classification Search
CPC ..... A61B 6/0407; A61B 6/5205; A61B 6/545; A61B 6/563; G06T 7/20; G06T 2207/100081; G06T 2207/20081; G06T 2207/20084; G06T 7/70; G06V 10/10; G06V 10/22; G06V 40/10
See application file for complete search history.

(56) References Cited

U.S. PATENT DOCUMENTS

| | | |
|---|---|---|
| 2004/0081341 A1 | 4/2004 | Cherek et al. |
| 2005/0256390 A1 | 11/2005 | Laux et al. |
| 2010/0284601 A1 | 11/2010 | Rubner et al. |
| 2011/0299747 A1 | 12/2011 | Solf et al. |
| 2012/0293846 A1 | 11/2012 | Wong et al. |
| 2013/0083894 A1 | 4/2013 | Niebler et al. |
| 2013/0102883 A1 | 4/2013 | Piferi et al. |
| 2013/0345573 A1 | 12/2013 | Kargar et al. |
| 2015/0104092 A1 | 4/2015 | Flohr et al. |
| 2015/0366527 A1 | 12/2015 | Yu et al. |
| 2017/0100089 A1 | 4/2017 | Chang et al. |
| 2017/0311921 A1 | 11/2017 | Feuerlein et al. |
| 2017/0354385 A1 | 12/2017 | Lerch |
| 2018/0268558 A1 | 9/2018 | Bauer et al. |
| 2018/0330496 A1 | 11/2018 | Ma et al. |
| 2018/0350078 A1 | 12/2018 | Sun et al. |
| 2020/0058389 A1 | 2/2020 | Saalbach et al. |

FOREIGN PATENT DOCUMENTS

| | | |
|---|---|---|
| CN | 103083022 A | 5/2013 |
| CN | 103142230 A | 6/2013 |
| CN | 103691064 A | 4/2014 |
| CN | 104000588 A | 8/2014 |
| CN | 104414677 A | 3/2015 |
| CN | 106388851 A | 2/2017 |
| CN | 106530280 A | 3/2017 |
| JP | 2005013489 A | 1/2005 |

OTHER PUBLICATIONS

Written Opinion for PCT/CN2017/088375 mailed on Feb. 26, 2018, 4 pages.

First Office Action in Chinese Application No. 201711222006.3 mailed on Feb. 3, 2020, 19 pages.

Yu, Xiao-E et al., The Measurement and Analysis of CT Mechanical Parameters, Journal of First Military Medical University, 20(5): 426-428, 2000.

IMAGING SYSTEMS AND METHODS THEREOF

CROSS-REFERENCE TO RELATED APPLICATIONS

This application is a continuation of U.S. patent application Ser. No. 16/950,889, filed on Nov. 17, 2020 which is a continuation of U.S. patent application Ser. No. 15/709,703 (now U.S. Pat. No. 10,856,832), filed on Sep. 20, 2017, which is a continuation of International Application No. PCT/CN2017/088375, filed on Jun. 15, 2017, the entire contents of each of which are hereby incorporated by reference.

TECHNICAL FIELD

The present disclosure generally relates to a system and method for imaging, and more particularly, to a system and method for automated medical imaging.

BACKGROUND

Medical imaging often requires accurate and repeatable positioning of a patient for diagnostic scanning and treatment. A table supporting the patient may need to be moved to appropriate positions during the scanning. The table is typically moved manually by an operator. Meanwhile, parameters of a scanner may need to be set manually by the operator for scanning the patient at various positions. These manual operations may be time-consuming and may result in inaccurate diagnosis. Therefore, it would be desirable to provide effective mechanisms for automated imaging.

SUMMARY

One aspect of the present disclosure relates to a method for imaging. The method may include one or more of the following operations. Image data of a target subject positioned on a scanning table may be acquired. First position information of the target subject may be determined by a processor based on the image data. Second position information related to a scan region of the target subject may be determined by the processor based on the image data. The target subject may be scanned using an imaging device based on the first position information and the second position information.

Another aspect of the present disclosure relates to a non-transitory computer-readable medium including executable instructions. The instructions, when executed by at least one processor, may cause the at least one processor to: acquire image data of a target subject positioned on a scanning table; determine first position information of the target subject based on the image data; determine second position information related to a scan region of the target subject based on the image data; and cause the target subject to be scanned by an imaging device based on the first position information and the second position information.

A further aspect of the present disclosure relates to an imaging system. The system may include at least one processor and instructions. When executing the instructions, the at least one processor is directed to: acquire image data of a target subject positioned on a scanning table; determine first position information of the target subject based on the image data; determine second position information related to a scan region of the target subject based on the image data; and cause the target subject to be scanned by an imaging device based on the first position information and the second position information.

In some embodiments, the first position information of the target subject may include a position of the target subject relative to the imaging device.

In some embodiments, the image data of the target subject may include a first image of the target subject and a second image of the target subject, wherein the first image of the target subject may correspond to a top view of the target subject, and wherein the second image of the target subject may correspond to a side view of the target subject.

In some embodiments, the determination of the second position information related to the scan region of the target subject may include one or more of the following operations. The scan region in at least one of the first image or the second image may be located.

In some embodiments, the determination of the first position information of the target subject may include one or more of the following operations. The image data may be processed using a first trained model, wherein the first trained model may be trained using a first plurality of training images corresponding to a plurality of positions of at least one sample subject.

In some embodiments, the determination of the second position information related to a scan region of the target subject based on the image data may include one or more of the following operations. A portion of the image data that corresponds to the scan region of the target subject may be determined. The second position information of the scan region may be determined based on the portion of the image data.

In some embodiments, the determination of the portion of the image data that corresponds to the scan region of the target subject may include one or more of the following operations. The image data may be processed using a second trained model, wherein the second trained model may be trained using a second plurality of training images corresponding to a plurality of sample scan regions of at least one sample subject.

In some embodiments, the determination of the portion of the image data that corresponds to the scan region of the target subject may include one or more of the following operations. A first candidate scan region may be determined based on a top view of the target subject. A second candidate scan region may be determined based on a side view of the target subject.

In some embodiments, the determination of the second position information of the scan region may include one or more of the following operations. A mapping relation between the portion of the image data and location information related to the imaging device may be determined. The second position information may be determined based on the mapping relation.

In some embodiments, the scanning of the target subject based on the first position information and the second position information may include one or more of the following operations. A distance for moving the scanning table may be determined based on the first position information and the second position information. The scanning table may be caused to be moved based on the distance.

In some embodiments, the scanning of the target subject based on the first position information and the second position information may include one or more of the following operations. A scan parameter may be set based on the first position information and the second position information of the target subject.

In some embodiments, the scanning of the target subject based on the first position information and the second position information may further include one or more of the following operations. A reconstruction parameter may be set based on the first position information and the second position information of the target subject.

In some embodiments, the method may further include one or more of the following operations. An image may be generated based on the scanning result and the reconstruction parameter.

In some embodiments, the generated image may meet a standard of the digital imaging and communications in medicine (DICOM).

In some embodiments, the first position information of the target subject may include at least one of a head first-prone position, a head first-supine position, a head first-decubitus right position, a head first-decubitus left position, a feet first-decubitus right position, a feet first-decubitus left position, a feet first-prone position, or a feet first-supine position.

In some embodiments, the imaging device may include a computed tomography scanner.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
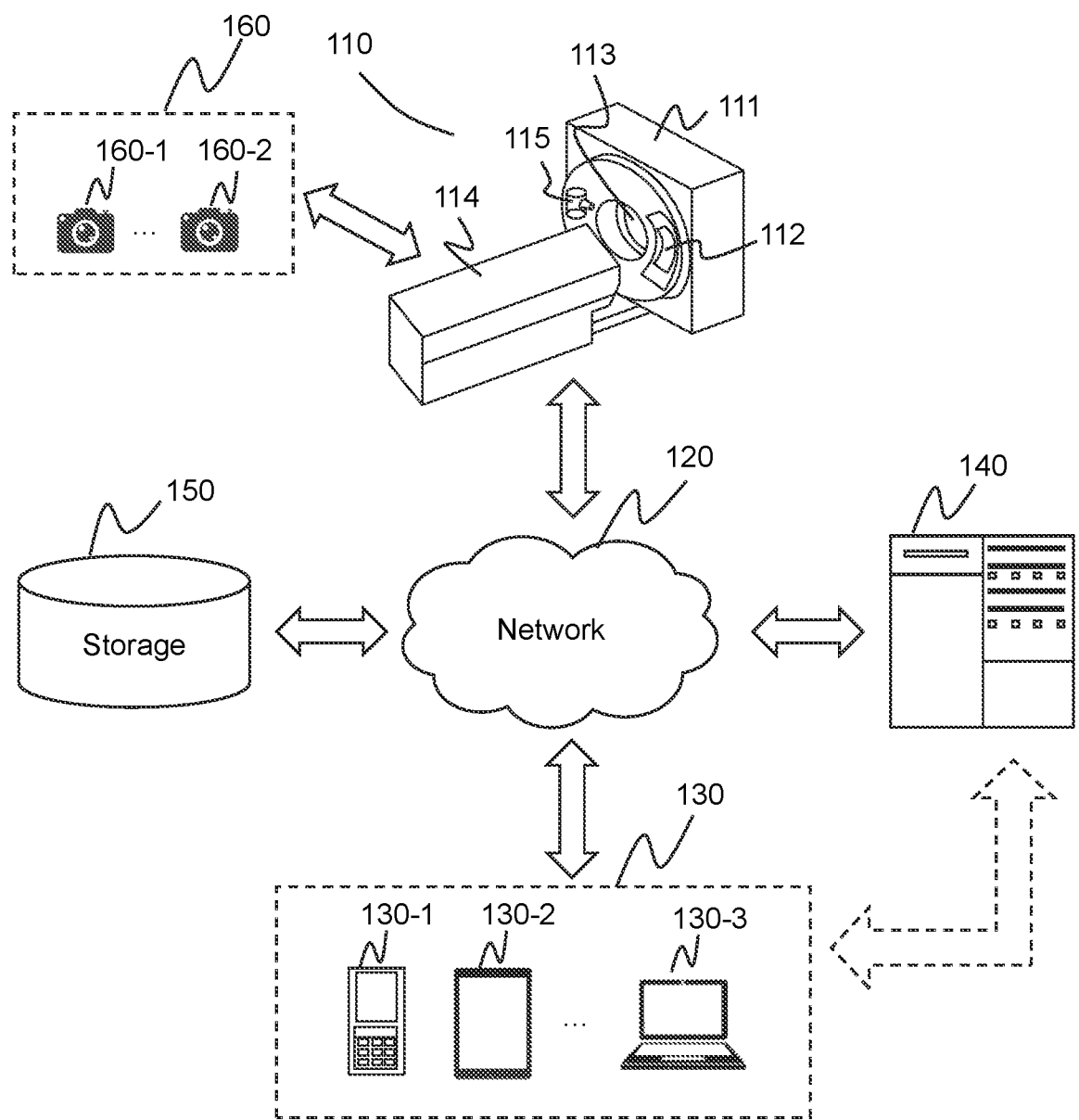
FIGS. 1A and 1B are schematic diagrams illustrating an exemplary imaging system according to some embodiments of the present disclosure.

In the following detailed description, numerous specific details are set forth by way of example in order to provide a thorough understanding of the relevant application. However, it should be apparent to those skilled in the art that the present application may be practiced without such details. In other instances, well-known methods, procedures, systems, components, and/or circuitry have been described at a relatively high-level, without detail, in order to avoid unnecessarily obscuring aspects of the present application. Various modifications to the disclosed embodiments will be readily apparent to those skilled in the art, and the general principles defined herein may be applied to other embodiments and applications without departing from the spirit and scope of the present application. Thus, the present application is not limited to the embodiments shown, but to be accorded the widest scope consistent with the claims.

It will be understood that when a unit, module or block is referred to as being "on," "connected to," "communicate with," "coupled to" another unit, module, or block, it may be directly on, connected or coupled to, or communicate with the other unit, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

An aspect of the present disclosure relates to a system and method for scanning a target subject. To scan the target subject, the system and method may acquire image data of the target subject, identify position information of the target subject, determine scanning information of the target subject, and/or control the scanning of the target subject. The system and method may determine the scanning information based on the position information of the target subject. Further, the system and method may realize automatic scanning based on automatic regulation of a position of a table supporting the target subject and a plurality of scanning parameters.

For illustration purposes, the following description is provided to help better understanding a scanning process. It is understood that this is not intended to limit the scope of the present disclosure. For persons having ordinary skills in the art, a certain amount of variations, changes and/or modifications may be deducted under guidance of the present disclosure. Those variations, changes and/or modifications do not depart from the scope of the present disclosure.

Figure 1B:
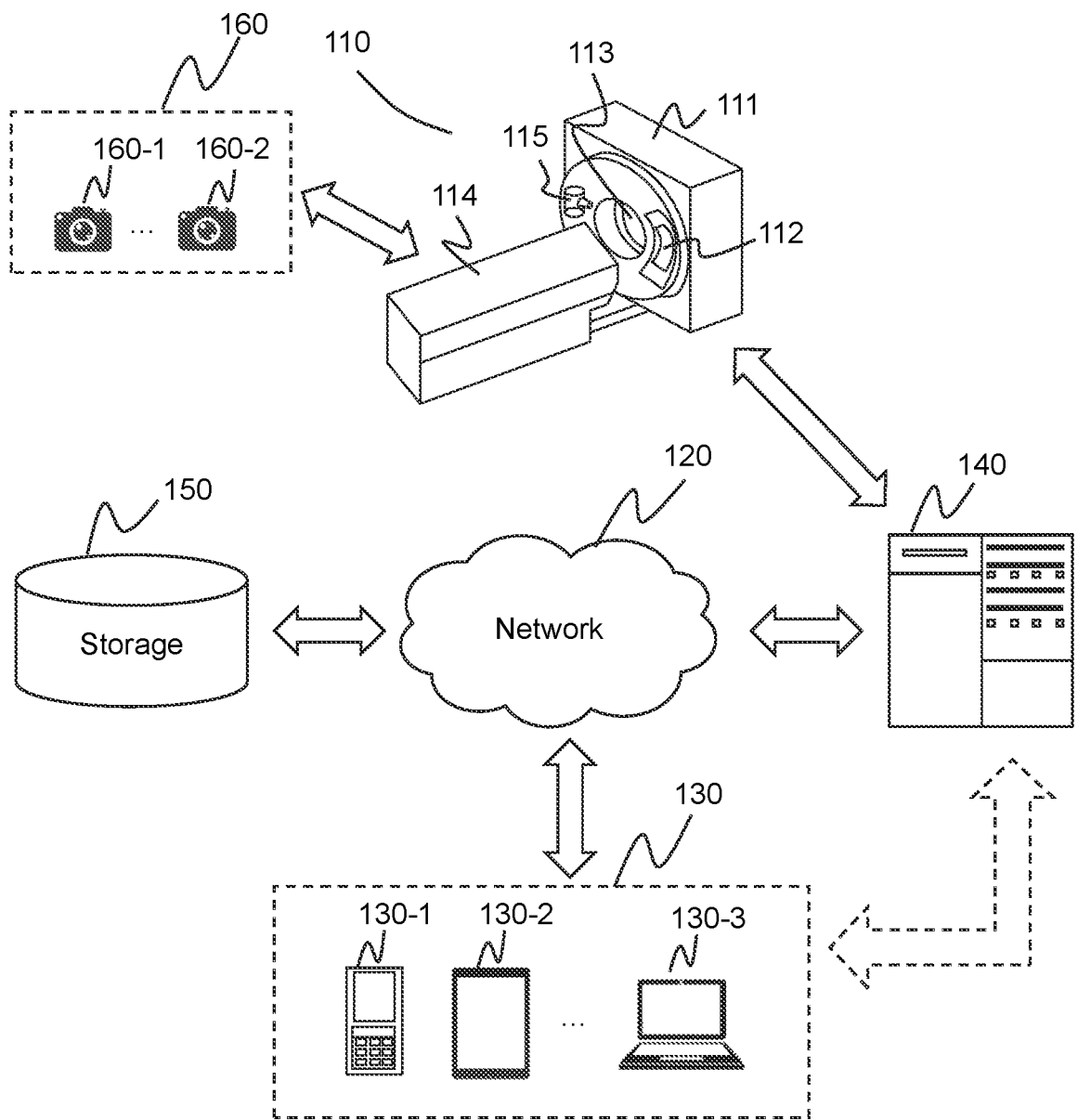

FIGS. 1A and 1B are schematic diagrams illustrating an exemplary imaging system 100 according to some embodiments of the present disclosure. As shown, the imaging system 100 may include a scanner 110, a network 120, one or more terminals 130, a processing engine 140, a storage 150, and one or more image acquisition devices 160. The connection between the components in the imaging system 100 may be variable. Merely by way of example, as illustrated in FIG. 1A, the scanner 110 may be connected to the processing engine 140 through the network 120. As another example, as illustrated in FIG. 1B, the scanner 110 may be connected to the processing engine 140 directly.

The scanner 110 (also referred to as an imaging device) may scan an object, and/or generate a plurality of data relating to the object. The scanner 110 may further reconstruct an image from the plurality of data. In some embodiments, the scanner 110 may be a medical imaging device, for example, a PET device, a SPECT device, a CT device, an MRI device, or the like, or any combination thereof (e.g., a PET-CT device, a PET-MRI device, or a CT-MRI device). The scanner 110 may include a gantry 111, a detector 112, a detecting region 113, and a scanning table 114. In some embodiments, the scanner 110 may also include a radioactive scanning source 115. The gantry 111 may support the detector 112 and the radioactive scanning source 115. A subject may be placed on the scanning table 114 for scanning. The radioactive scanning source 115 may emit radioactive rays to the subject. The detector 112 may detect radiation events (e.g., gamma photons) emitted from the detecting region 113. In some embodiments, the detector 112 may include one or more detector units. The detector units may include a scintillationdetector (e.g., a cesium iodide detector), a gas detector, etc. The detector unit may be and/or include a single-row detector and/or a multi-rows detector.

The network 120 may include any suitable network that can facilitate exchange of information and/or data for the imaging system 100. In some embodiments, one or more components of the imaging system 100 (e.g., the scanner 110, the terminal 130, the processing engine 140, the storage 150, the image acquisition device(s) 160, etc.) may communicate information and/or data with one or more other components of the imaging system 100 via the network 120. For example, the processing engine 140 may obtain image data from the scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

In some embodiments, the scanner 110, the processing engine 140, and/or the storage 150 may be directly connected with each other. The scanner 110, the processing engine 140, and/or the storage 150 may not communicate with each other via the network 120.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

Figure 2:
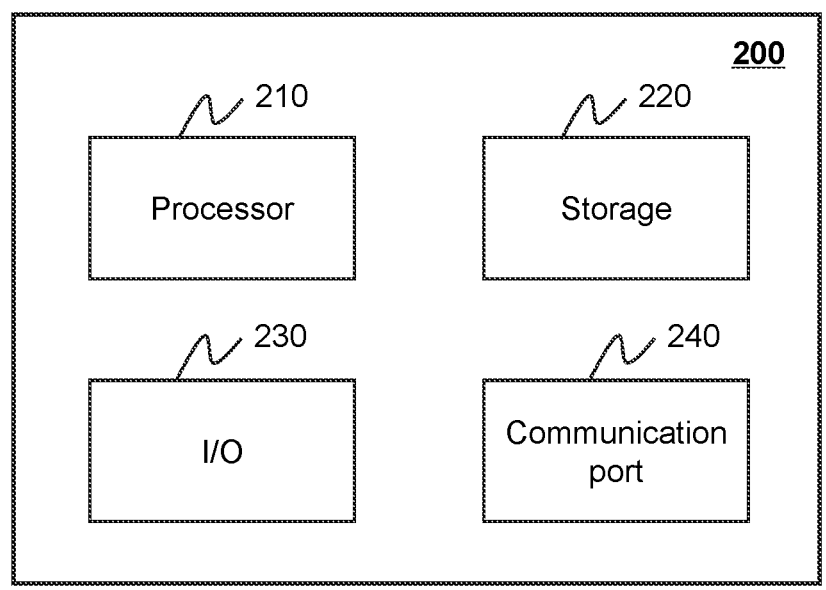
FIG. 2 is a schematic diagram illustrating exemplary hardware and/or software components of an exemplary computing device on which the processing engine may be implemented according to some embodiments of the present disclosure.

The processing engine 140 may control the scanner 110 for scanning. For example, the processing engine 140 may control movement of the scanning table 114. As another example, the processing engine 140 may control the radioactive scanning source 115 to emit X-rays. The processing engine 140 may process data and/or information obtained from the scanner 110, the terminal 130, and/or the storage 150. For example, the processing engine 140 may process image data and determine a regularization item that may be used to modify the image data. In some embodiments, the processing engine 140 may be a single server or a server group. The server group may be centralized or distributed. In some embodiments, the processing engine 140 may be local or remote. For example, the processing engine 140 may access information and/or data stored in the scanner 110, the terminal 130, and/or the storage 150 via the network 120. As another example, the processing engine 140 may be directly connected to the scanner 110, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the imaging system 100 (e.g., the processing engine 140, the terminal 130, the image acquisition device 160, etc.). One or more components in the imaging system 100 may access the data or instructions stored in the storage 150 via the network 120. In some embodiments, the storage 150 may be directly connected to or communicate with one or more other components in the imaging system 100 (e.g., the processing engine 140, the terminal 130, the image acquisition device 160, etc.). In some embodiments, the storage 150 may be part of the processing engine 140.

The image acquisition device(s) 160 may acquire one or more images of a target subject positioned on the scanning table 114. The image acquisition device(s) 160 may acquire the image(s) of the target subject from various directions. The acquired images may be recorded as image data. In some embodiments, an acquired image may show a top view of the target subject. In some embodiments, an acquired image may show a side view of the target subject. The image acquisition device(s) 160 may be and/or include one or more cameras, video recorders, or any other device that may acquire an image. The image acquisition device(s) 160 may include a first acquisition device 160-1, a second acquisition device 160-2, or the like, or any combination thereof. The first acquisition device 160-1 and the second acquisition device 160-2 may be two devices of the same type or different types.

In some embodiments, the image acquisition device(s) 160 may be fixed on the scanner 110 or mounted in a fixed position around the scanner 110. For example, the image acquisition device(s) 160 may be fixed on an inner wall of the gantry 111 to be exposed to the detecting region 113. In some embodiments, the image acquisition device(s) 160 may be movable. For example, the image acquisition device(s) 160 may be mounted on a mobile equipment to move around the scanner 110. In some embodiments, the image acquisition device(s) 160 may be movable while being fixed on the scanner 110. For example, the image acquisition device(s) 160 may be fixed on the inner wall of the gantry 111, and rotate in the detecting region 113 with the gantry 111, so that the image acquisition device(s) 160 may acquire images of different views from different directions.

In some embodiments, the image acquisition device(s) 160 may be connected to the network 120 to communicate with one or more other components in the imaging system 100 (e.g., the processing engine 140, the terminal 130, the storage 150, etc.). In some embodiments, the image acquisition device(s) 160 may include a storage for storing the image data it acquires. One or more components in the imaging system 100 (e.g., the processing engine 140) may access the image data stored in the storage via the network 120.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data obtained from the scanner 110, the terminal 130, the storage 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the scanner 110, the terminal 130, the storage 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the scanner 110, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
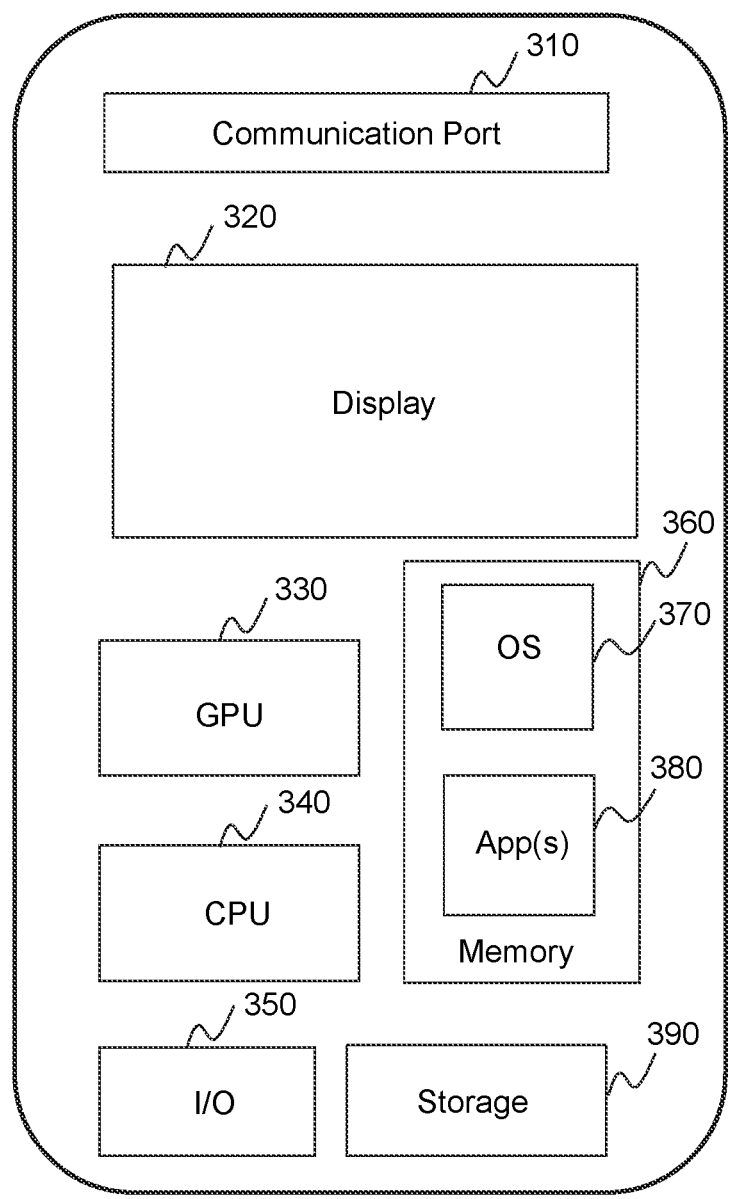
FIG. 3 is a schematic diagram illustrating exemplary hardware and/or software components of an exemplary mobile device on which the terminal may be implemented according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
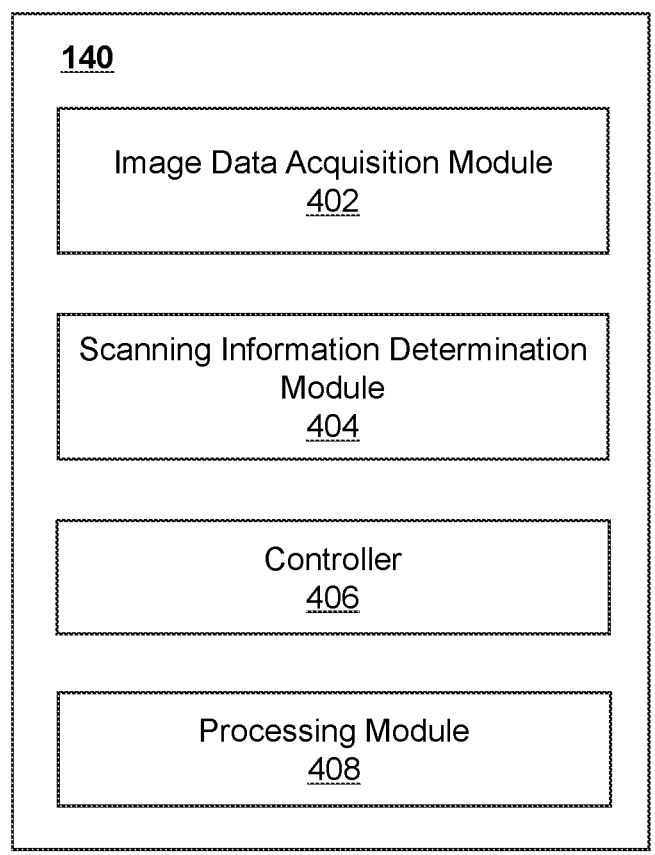
FIG. 4 is a schematic diagram illustrating an exemplary processing engine according to some embodiments of the present disclosure.

FIG. 4 is a schematic diagram illustrating an exemplary processing engine 140 according to some embodiments of the present disclosure. The processing engine 140 may include an image data acquisition module 402, a scanning information determination module 404, a controller 406, and a processing module 408.

The image data acquisition module 402 may acquire image data of a target subject. The image data may include one or more images (e.g., still images, moving images, two-dimensional images, three-dimensional images, etc.), encoding parameters, decoding parameters, and/or any other data about one or more images. The image data may be associated with one or more parts of the target subject. In some embodiments, the image data may be associated with a whole body of the target subject. In some embodiments, the image data may include information regarding a portion of the target subject, for example, an upper body, a lower body, etc. In some embodiments, the image data may include information regarding a position of the target subject relative to the scanner 110. In some embodiments, the image data acquisition module 402 may acquire the image data from the image acquisition device(s) 160, the storage 150, an external data source, and/or any other device that is capable of providing image data.

Figure 5:
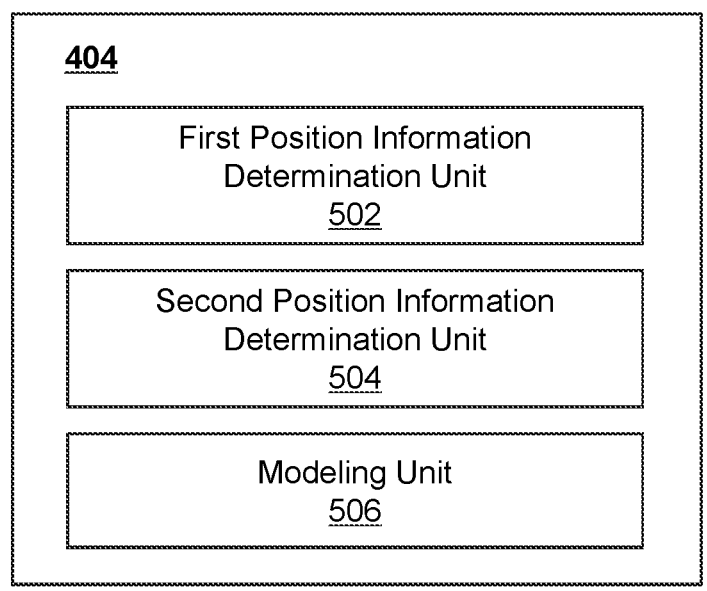
FIG. 5 is a schematic diagram illustrating an exemplary scanning information determination module according to some embodiments of the present disclosure.

The scanning information determination module 404 may determine scanning information. The scanning information determination module 404 may include one or more units as illustrated in FIG. 5. The scanning information may include information that may be used in imaging and/or scanning. In some embodiments, the scanning information may include information associated with the target subject, a relative position relationship between the target subject and the scanner 110, or the like, or any combination thereof. In some embodiments, the scanning information determination module 404 may determine the scanning information based on position information of the target subject. The position information of the target subject may include, for example, a position of the target subject recognized by the scanner 110. The scanning information determination module 404 may determine the scanning information based on image data related to the target subject (e.g., the image data acquired by the image data acquisition module 402).

Figure 6:
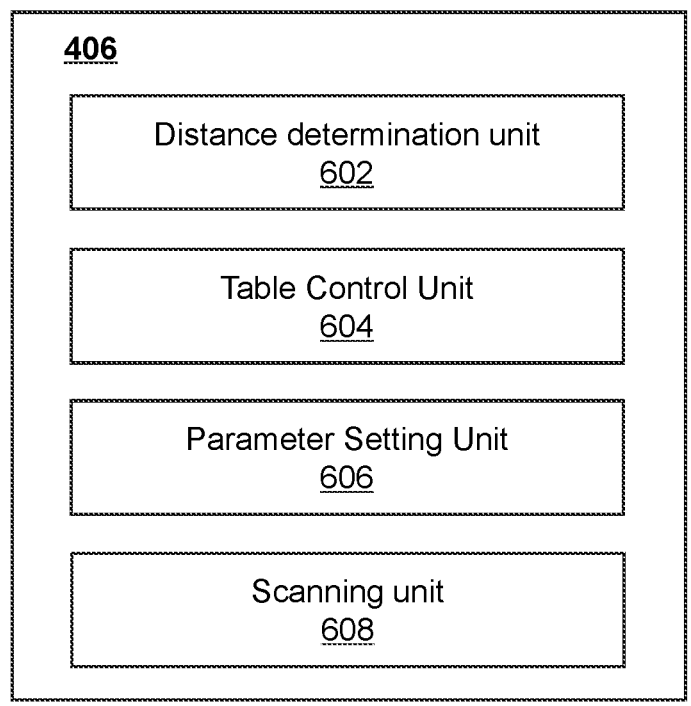
FIG. 6 is a schematic diagram illustrating an exemplary controller according to some embodiments of the present disclosure.

The controller 406 may control the scanning of the target subject based on the scanning information determined by the scanning information determination module 404. In some embodiments, the controller may include one or more units as illustrated in FIG. 6. In some embodiments, the controller 406 can control the scanning by controlling movement of the scanning table 114, setting scanning parameters, or the like, or any combination thereof.

The processing module 408 may process information provided by various modules of the processing engine 140. The processing module 408 may process image data acquired by the image data acquisition module 402, scanning information determined by the scanning information determination module 402, etc. In some embodiments, the processing module 408 may reconstruct one or more images based on an imaging and/or scanning result according to a reconstruction technique, generate reports including one or more images and/or other related information, and/or perform any other function for image reconstruction in accordance with various embodiments of the present disclosure. The reconstruction technique may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

FIG. 5 is a schematic diagram illustrating an exemplary scanning information determination module 404 according to some embodiments of the present disclosure. The scanning information determination module 404 may include a first position information determination unit 502, a second position information determination unit 504, and a modeling unit 506.

The first position information determination unit 502 may determine position information of the target subject (also referred to as the "first position information"). The first position information may be include information about a position (e.g., a posture, an orientation, etc.) of the target subject relative to the scanner 110. For example, the first position information may include one or more coordinates, angles, etc. that can represent the position of the target subject. In some embodiments, the position of the target subject relative to the scanner 110 can include and/or be one or more known positions, such as a head first-prone position, a head first-supine position, a head first-decubitus right position, a head first-decubitus left position, a feet first-decubitus right position, a feet first-decubitus left position, a feet first-prone position, a feet first-supine position, etc. A head first-prone position may refer to a position in which the target subject's head is positioned towards a front of the scanner 110 and the target subject's face is positioned in a downward (gravity) direction. A head first-supine position may refer to a position in which the target subject's head is positioned towards the front of the scanner 110 and the target subject's face is positioned in an upward direction. A head first-decubitus right position may refer to a position in which the target subject's head is positioned towards the front of the scanner 110 and the target subject's right side is positioned in a downward direction. A head first-decubitus left position may refer to a position in which the target subject's head is positioned towards the front of the scanner 110 and the target subject's left side is positioned in a downward direction. A feet first-decubitus right position may refer to a position in which the target subject's feet is positioned towards the front of the scanner 110 and the target subject's right side is positioned in a downward direction. A feet first-decubitus left position may refer to a position in which the target subject's feet is positioned towards the front of the scanner 110 and the target subject's left side is positioned in a downward direction. A feet first-prone position may refer to a position in which the target subject's feet is positioned towards the front of the scanner 110 and the target subject's face is positioned in a downward (gravity) direction. A feet first-supine position may refer to a position in which the target subject's feet is positioned towards the front of the scanner 110 and the subject's face is positioned in an upward direction. The front of the scanner 110 may refer to a front side of the scanner 110 in which the scanning table 114 may enter the detecting region 113. In some embodiments, the first position information determination module 502 may determine the first position information using one or more deep learning techniques (e.g., by performing one or more operations as described in connection with FIG. 7).

The second position information determination unit 504 may determine position information of a scan region of the target subject (also referred to as the "second position information"). In some embodiments, the scan region may refer to a region of the target subject to be scanned by the scanner 110. The scan region may include one or more portions of the target subject, for example, a head, a foot, a chest, an abdomen, an organ (e.g., a brain, a lung, a liver, a stomach, a rib, a vertebra, etc.), or the like, or any combination thereof. The second position information of the scan region of the target subject may include information about a position of the scan region relative to the scanner 110. For example, the second position information can include one or more coordinates, angles, etc. representative of the position of the scan region. In some embodiments, the second position information determination module 504 may determine the second position information using one or more deep learning techniques (e.g., by performing one or more operations described in connection with FIG. 7).

The modeling unit 506 may establish one or more models for processing the image data. A model may refer to an algorithm that may process the image data for determining scanning information. In some embodiments, the modeling unit 506 may establish the model(s) using deep learning. In some embodiments, the modeling unit 506 may establish a first trained model for determining the first position information and/or a second trained model for determining the second position information.

The first trained model may be trained using a first plurality of training images corresponding to a plurality of positions of one or more sample subjects. The first trained model may classify the image data (e.g., the image data acquired by the image data acquisition module 402) into one or more groups. Each of the groups may correspond to one or more known positions. In some embodiments, each of the groups corresponds to a known position. For example, image data corresponding to the head first-prone position of the target subject may be classified into a group corresponding to the head first-prone position. As another example, image data corresponding to an abnormal position of the target subject may be classified into a group corresponding to an abnormal position, and the target subject may need to be positioned again.

The second trained model may be trained using a second plurality of training images corresponding to a plurality of sample scan regions of one or more sample subjects. The second trained model may identify which portion of the image data (e.g., the image data acquired by the image data acquisition module 402) corresponds to the scan region and/or which portion of the image data does not correspond to the scan region. In some embodiments, the second trained model may identify portion(s) corresponding to the scan region in different images taken from different view directions of the target subject. For example, if the target subject's stomach is to be scanned, a portion corresponding to the stomach in an image taken from a top view of the target subject may be identified, and a portion corresponding to the stomach in an image taken from a side view of the target subject may be identified.

It should be noted that the above description of the scanning information determination module 404 is merely provided for the purpose of illustration, and not intended to limit the scope of the present disclosure. For persons having ordinary skills in the art, multiple variations and modifications may be made to the scanning information determination module 404 under the teachings of the present disclosure. However, those variations and modifications do not depart from the scope of the present disclosure. For example, the modeling unit 506, the first position information determination unit 502, and/or the second position information determination unit 504 may be combined into a single unit. As another example, the modeling unit 506 may be removed, and the models for processing image data may be acquired from the storage 150 or an external data source.

FIG. 6 is a schematic diagram illustrating an exemplary controller 406 according to some embodiments of the present disclosure. The controller 406 may include a distance determination unit 602, a table control unit 604, a parameter setting unit 606, and a scanning unit 608.

The distance determination unit 602 may determine one or more distances, directions, or any other parameter for adjusting the position of the scanning table 114 to place the scan region of the target subject at one or more positions in the detecting region 113 for scanning. The position of the scanning table 114 can be adjusted by, for example, moving the scanning table 114 according to the distance(s), directions, and/or any other parameter. In some embodiments, the distance determining unit 602 may determine the distance(s) based on the second position information.

In some embodiments, the distance determination unit 602 may determine one or more moving directions for moving the scanning table 114. The moving direction(s) may include a direction parallel to the scanning table 114, a direction perpendicular to the scanning table 114, or the like, or any combination thereof. The direction parallel to the scanning table 114 may include a direction from a head to a tail of the scanning table 114 (or vice versa) and/or a direction from a left side to a right side of the scanning table 114 (or vice versa). In some embodiments, the moving direction may be a comprehensive direction of the parallel direction(s) and the perpendicular direction. In some embodiments, the target subject may change positions on the scanning table 114 during the scanning, thus the distance determination unit 602 may re-determine the distance(s), moving direction(s) and/or any other parameter for moving the scanning table 114.

The table control unit 604 may control motions of the scanning table 114 based on the distance(s), moving direction(s), and/or any other parameter determined by the distance determining unit 602. The table control unit 604 may generate a control signal based on the distance(s), moving direction(s), and/or any other parameter for moving the scanning table 114, and transmit the control signal to the scanning table 114, so that the scanning table 114 may move automatically for a certain distance in one or more certain directions. Further, the scan region of the target subject may be placed at a position in the detecting region 113 for scanning. In some embodiments, the table control unit 604 may control a speed of the scanning table 114 while moving the scanning table 114.

The parameter setting unit 606 may set one or more scanning parameters and/or one or more reconstruction parameters. The scanning parameter(s) may be related to a scanning result of the target subject using the scanner 110. The reconstruction parameter(s) may be related to image reconstruction. For a CT scanning, the scanning parameters may include a scanning type, a tube voltage, a tube current, a scanning time, a field of view, a matrix, a collimation, an acquisition channel, a slice thickness, a slice gap, a pitch, a rotation speed, a cardiac gating, a reconstruction algorithm, or the like, or any combination thereof. The reconstruction parameters may include an image resolution, a reconstruction interval, a kernel, a filter, one or more parameters used in a reconstruction technique (e.g., an iteration time in iterative reconstruction, a coefficient, a threshold, etc.), or the like, or any combination thereof. In some embodiments, the parameter setting unit 606 may set one or more scanning parameters and/or one or more reconstruction parameters based on the first position information determined by the first position information determination unit 502 and/or the second position information determined by the second position information determination unit 504. In some embodiments, the parameter setting unit 606 may set one or more scanning parameters and/or one or more reconstruction parameters based on a scanning protocol. The scanning protocol may be acquired from the storage 150 or an external data source. In some embodiments, the scanning protocol may be loaded to the processing engine 140 by a user, so that the parameter setting unit 606 may receive the scanning protocol and automatically set the scanning parameter(s) and/or reconstruction parameter(s).

The scanning unit 608 may scan the target subject. In some embodiments, the scanning unit 608 may scan one or more portions of the target subject, for example, a head, a foot, a chest, an abdomen, an organ (e.g., a brain, a lung, a liver, a stomach, a rib, a vertebra, etc.), or the like, or any combination thereof. The scanning unit 608 may generate one or more control signals based on the scanning parameter(s), and transmit the control signal(s) to the scanner 110 to conduct image scanning. In some embodiments, the processor 210 and/or CPU 340 may issue one or more instructions and/or transmit information (e.g., the scanning parameter(s)) to cause the scanner 110 to scan the target subject based on the instruction(s) and/or scanning parameter(s). For example, the processor 210 and/or CPU 340 may issue the instruction(s) to the scanning unit 608, obtain scanning parameter(s) and/or reconstruction parameter(s) from the parameter setting unit 606, transmit the scanning parameter(s) to the scanning unit 608, cause the scanner 110 to scan the target subject, transmit the reconstruction parameter(s) to the processing module 408, and cause the processing module 408 to reconstruct an image based on a scanning result.

It should be noted that the above description of the controller 406 is merely provided for the purpose of illustration, and not intended to limit the scope of the present disclosure. For persons having ordinary skills in the art, multiple variations and modifications may be made to the controller 406 under the teachings of the present disclosure. However, those variations and modifications do not depart from the scope of the present disclosure. For example, the distance determination unit 602 and the table control unit 604 may be combined into a single unit. As another example, the table control unit 604 and the scanning unit 608 may be combined into a single unit.

Figure 7:
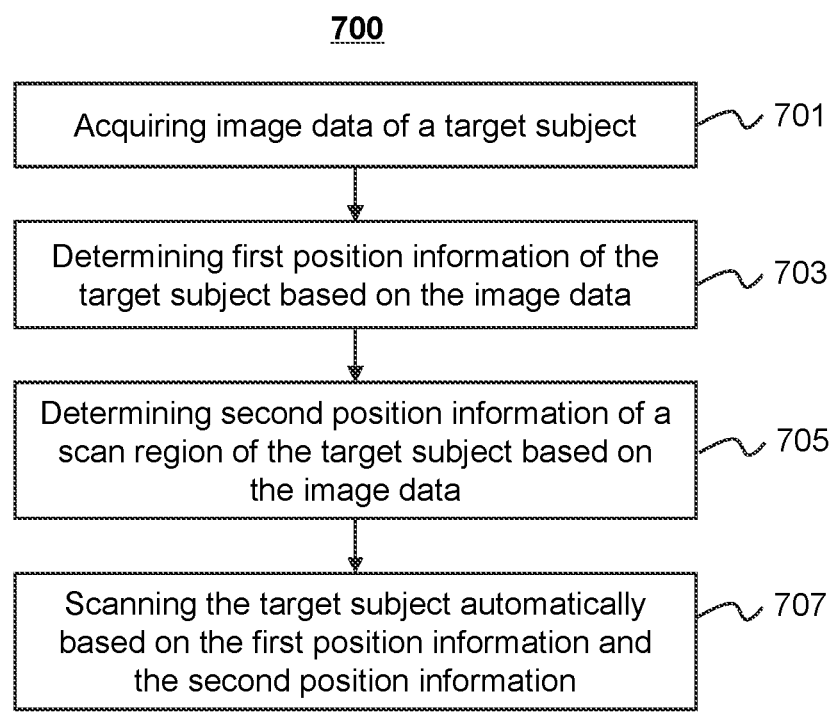
FIG. 7 is a flowchart illustrating an exemplary process for scanning a target subject according to some embodiments of the present disclosure.

FIG. 7 is a flowchart illustrating an exemplary process 700 for scanning a target subject according to some embodiments of the present disclosure. In some embodiments, the process 700 may be performed by the processing engine 140.

In 701, image data of a target subject may be acquired. In some embodiments, the image data may be acquired by the image data acquisition module 402. The image data may be associated with one or more parts of the target subject. In some embodiments, the image data may be associated with a whole body of the subject. In some embodiments, the image data may include information regarding a portion of the target subject, for example, an upper body, a lower body, etc. In some embodiments, the image data may correspond to an image showing a posture of the target subject lying on the scanning table 114. In some embodiments, the image data may be acquired from the storage 150 or an external data source.

In some embodiments, the image data may be acquired from the image acquisition device(s) 160. In some embodiments, the image data may include images representative of various views of the target subject. In some embodiments, the image data acquired in 701 may include a first image of the target subject and a second image of the target subject. The first image and the second image may correspond to a top view of the target subject and a side view of the target subject, respectively. In some embodiments, the first image and the second image may be acquired by two different image acquisition devices 160. For example, the first image may be acquired by a first acquisition device 160-1 placed over the scanning table 114 at a first distance from the scanning table 114 (e.g., a first acquisition device 160-1 fixed on the inner wall of the gantry 111 and right above the scanning table 114). The second image may be acquired by a second acquisition device 160-2 placed in a horizontal direction of the scanning table 114 at a second distance from the scanning table 114 (e.g., a second acquisition device 160-2 fixed on the inner wall of the gantry 111 and parallel to the scanning table 114). In some embodiments, the first image and the second image may be acquired by the same image acquisition device 160. For example, the first image may be acquired by the image acquisition device 160 fixed on the inner wall of the gantry 111 when the image acquisition device 160 rotates to a first place right above the scanning table 114. While the second image may be acquired by the same image acquisition device 160 when the image acquisition device 160 rotates to a second place parallel to the scanning table 114.

In 703, first position information of the target subject may be determined based on the image data acquired in 701. In some embodiments, the first position information may be determined by the first position information determination unit 502. The first position information may include a first position (e.g., a posture) of the target subject relative to the scanner 110. The first position may be one of a plurality of known positions (e.g., the positions described in connection with FIG. 5).

The first position information may be determined using a first trained model. The first trained model may be trained using a first plurality of training images corresponding to a plurality of positions of one or more sample subjects. In some embodiments, the sample subject(s) may have different body shapes and/or body sizes. For example, the sample subject(s) may include a girl, a boy, an adult woman, an adult man, an elderly woman, an elderly man, or the like, or any combination thereof. In some embodiments, the first plurality of training images may include positive training images and negative training images. The positive training images may refer to images corresponding to the known positions described above. The negative training images may refer to images that do not correspond to the known positions. For example, the negative training images may include an image of a seated sample subject, an image of a standing sample subject, an image of an incorrectly positioned sample subject, or the like, or any combination thereof. The first plurality of training images may be acquired from the image acquisition device(s) 160, the storage 150, or an external data source.

In some embodiments, a first deep learning model including a first multilayer structure may be employed for training the first model. The first deep learning model may include, for example, deep neural networks, deep belief networks, convolutional neural networks, convolutional deep belief networks, deep Boltzmann machines, stacked auto-encoders, deep stacking networks, deep coding networks, deep kernel machines, or the like, or any combination thereof. In some embodiments, one or more features may be extracted from the first plurality of training images corresponding to different known positions. A feature of an image may refer to characteristic structural information associated with at least one portion of the image. An initial layer of the first multilayer structure may learn the feature(s) extracted from the training images, and the learned feature(s) may serve as input data for a next layer. Other layers of the first multilayer structure may learn one or more features in its input data obtained from its previous layer. The first multilayer structure may be modified based on the learning of each layer to obtain the first trained model. The first trained model may classify the image data acquired in 701 into one or more groups. Each of the groups may correspond to one or more known positions. In some embodiments, each of the groups corresponds to a known position. For example, image data corresponding to the head first-prone position of the target subject may be classified into a group corresponding to the head first-prone position. As another example, image data corresponding to an abnormal position of the target subject may be classified into a group corresponding to an abnormal position, and the target subject may need to be positioned again.

In 705, second position information of a scan region of the target subject may be determined based on the image data acquired in 701. In some embodiments, 705 may be performed by the second position information determination unit 504. A scan region may include a target region to be scanned by the scanner 110. The scan region may include one or more portions of the target subject, for example, a head, a foot, a chest, an abdomen, an organ (e.g., a brain, a lung, a liver, a stomach, a rib, a vertebra, etc.), or the like, or any combination thereof. In some embodiments, a first candidate scan region may be determined based on a top view of the target subject acquired in 701. In some embodiments, a second candidate scan region may be determined based on a side view of the target subject acquired in 701. In some embodiments, a portion of the image data that corresponds to the scan region of the target subject may be determined. Further, the second position information of the scan region may be determined based on the portion of the image data. In some embodiments, a mapping relation between the portion of the image data and location information related to the scanner 110 may be established. Further, the second position information may be determined based on the mapping relation. The mapping relation may refer to a mathematical relation (e.g., a function, or the like) that can transform the location of the scan region in the image data into location information of the scan region in the scanner 110.

In some embodiments, the portion of the image data that corresponds to the scan region may be determined using a second trained model. The second trained model may be trained using a second plurality of training images corresponding to a plurality of sample scan regions of one or more sample subjects. The second plurality of training images may be acquired from the image acquisition device(s) 160, the storage 150, or an external data source. In some embodiments, the second plurality of training images may include images representative of a top view of the sample subject(s) and/or images representative of a side view of the sample subject(s).

In some embodiments, a second deep learning model including a second multilayer structure may be employed for training the second model. The second deep learning model may include, for example, deep neural networks, deep belief networks, convolutional neural networks, convolutional deep belief networks, deep Boltzmann machines, stacked auto-encoders, deep stacking networks, deep coding networks, deep kernel machines, or the like, or any combination thereof. In some embodiments, one or more features may be extracted from the second plurality of training images. The feature(s) may include scan region feature(s) and non-scan region feature(s). An initial layer of the second multilayer structure may learn the scan region feature(s) and non-scan region feature(s), then the learned feature(s) may serve as input data for a next layer. Other layers of the second multilayer structure may learn one or more features in its input data obtained from its previous layer. The second multilayer structure may be modified based on the learning of each layer to obtain the second trained model. The second trained model may identify which portion of the image data acquired in 701 corresponds to the scan region and/or which portion of the image data does not correspond to the scan region. In some embodiments, the second trained model may identify portion(s) corresponding to the scan region in different images taken from different view directions of the target subject. For example, if the target subject's stomach is to be scanned, a portion corresponding to the stomach in an image taken from a top view of the target subject may be identified, and a portion corresponding to the stomach in an image taken from a side view of the target subject may be identified. The top view image and/or the side view image may be obtained as described in 701.

In some embodiments, the second position information of the scan region of the target subject may be determined based on marking information in the image data acquired in 701. In some embodiments, one or more markers (e.g., a ruler, a regular geometry) may be labelled or placed in the scanning table 114 (e.g., close to the target subject). The position of the marker(s) in the scanning table 114 may be predetermined. The marker(s) and the target subject may be acquired by the image acquisition device(s) 160 in the same image, so that the relative position of the target subject and the marker(s) may be determined based on the image. Further, the relative position of the target subject and the scanning table 114 may be determined. In some embodiments, the relative position of the scanning table 114 in the scanner 110 may be determined by the controller 406, and thus the second position information of the scan region of the target subject may be determined based on a first relative position and a second relative position. The first relative position may include the relative position of the target subject and the scanning table 114. The second relative position may include the relative position of the scanning table 114 in the scanner 110.

In 707, the target subject may be automatically scanned based on the first position information determined in 703 and the second position information determined in 705. In some embodiments, 707 may be performed by the controller 406. In some embodiments, the target subject may be automatically scanned by performing one or more operations described in connection with FIG. 8.

It should be noted that the above description about the process 700 for scanning the target subject is merely provided for the purpose of illustration, and not intended to limit the scope of the present disclosure. For persons having ordinary skills in the art, multiple variations and/or modifications may be made under the teachings of the present disclosure. However, those variations and modifications do not depart from the scope of the present disclosure. For example, 703 may be performed after or simultaneously with 705. One or more other operations may be added to process 700, or one or more operations may be omitted from process 700. For example, an operation for positioning the subject may be added before 701, which may be performed automatically or under a guidance of an operator (e.g., a doctor, a radiographer, etc.). As another example, an operation for storing data may be added between or after 701, 703, and/or 705. The data may be stored in the storage 150, the storage 220, the storage 390, or an external database (not shown).

Figure 8:
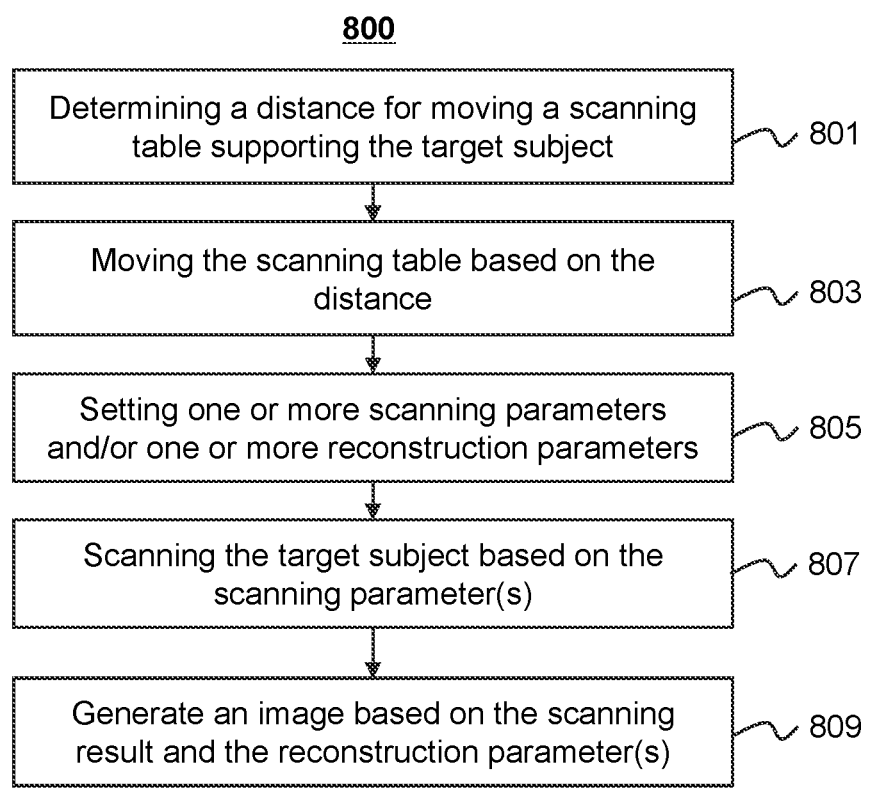
FIG. 8 is a flowchart illustrating an exemplary process for controlling image scanning according to some embodiments of the present disclosure.

FIG. 8 is a flowchart illustrating an exemplary process 800 for controlling image scanning according to some embodiments of the present disclosure. In some embodiments, the process 800 may be performed by the controller 406.

In 801, one or more distances, moving directions, and/or any other parameter for adjusting the position of the scanning table 114 may be determined. In some embodiments, the distance(s), moving direction(s), and/or any other parameter may be determined to place the scan region of the target subject at one or more positions in the detecting region 113 for scanning. The position of the scanning table 114 can be adjusted by, for example, moving the scanning table 114 according to the distance(s), direction(s), and/or any other parameter. In some embodiments, the distance(s), moving direction(s), and/or any other parameter may be performed by the distance determination unit 602. In some embodiments, the distance may be determined based on the second position information. The moving directions may include a direction parallel to the scanning table 114, a direction perpendicular to the scanning table 114, or the like, or any combination thereof. The second position information may indicate a current position of the scan region relative to the scanner 110. To obtain a qualified scanning result, the scan region may need to be moved to a target position. In some embodiments, the target position may be preset based on a scanning protocol or manual input. Further, the distance(s), the moving direction(s), and/or any other parameter may be determined based on a comparison of the second position information and the target position. In some embodiments, the target subject may change positions on the scanning table 114 during the scanning, and thus the distance(s), the moving direction(s), and/or any other parameter may be re-determined for moving the scanning table.

In 803, the scanning table 114 may be moved based on the distance(s), direction(s), and/or any other parameter determined in 801. Thus the scan region of the target subject may be placed at a target position in the detecting region 113 for scanning. In some embodiments, the scanning table 114 may be moved by the table control unit 604.

In 805, one or more scanning parameters and/or one or more reconstruction parameter(s) may be set. In some embodiments, operation 805 may be performed by the parameter setting unit 606. The scanning parameter(s) may be associated with a scanning result of the target subject using the scanner 110. The reconstruction parameter(s) may be related to image reconstruction. For a CT scanning, the scanning parameters may include a scanning type, a tube voltage, a tube current, a scanning time, a field of view, a matrix, a collimation, an acquisition channel, a slice thickness, a slice gap, a pitch, a rotation speed, a cardiac gating, a reconstruction algorithm, or the like, or any combination thereof. The reconstruction parameters may include an image resolution, a reconstruction interval, a kernel, a filter, one or more parameters used in a reconstruction technique (e.g., an iteration time in iterative reconstruction, a coefficient, a threshold, etc.), or the like, or any combination thereof. In some embodiments, the scanning parameter(s) and/or the reconstruction parameter(s) may be set based on the first position information determined in 703 and/or the second position information determined in 705. For example, the field of view for the scanning may be set based on the second position information associated with the scan region of the target subject. In some embodiments, the scanning parameter(s) and/or the reconstruction parameter(s) may be set automatically, semi-automatically, or manually. For example, the scanning parameters and/or the reconstruction parameter(s) may be automatically set based on the first position information determined in 703, the second position information determined in 705, and/or a scanning protocol. As another example, a user may set the scanning parameters and/or the reconstruction parameter(s) through the I/O 230. As a further example, the user may modify or adjust the automatically set scanning parameters and/or reconstruction parameter(s).

In 807, the target subject may be scanned based on the scanning parameter(s) set in 805. In some embodiments, the target subject may be scanned by the scanning unit 608. In some embodiments, the scan region of the target subject determined in 705 may be scanned. In some embodiments, one or more control signals may be generated based on the scanning parameters set in 805. The control signal(s) may be transmitted to the scanner 110 to conduct scanning.

In 809, an image may be generated based on the scanning result obtained in 807 and the reconstruction parameter(s) set in 805. In some embodiments, the generated image may be a standard image. The standard image may meet certain criteria, for example, a standard of the digital imaging and communications in medicine (DICOM).

It should be noted that the above description about the process 800 for controlling image scanning is merely provided for the purpose of illustration, and not intended to limit the scope of the present disclosure. For persons having ordinary skills in the art, multiple variations and/or modifications may be made under the teachings of the present disclosure. However, those variations and modifications do not depart from the scope of the present disclosure. For example, 805 may be performed before 801. One or more other operations may be added to process 800, or one or more operations may be omitted from process 800.

Figure 9:
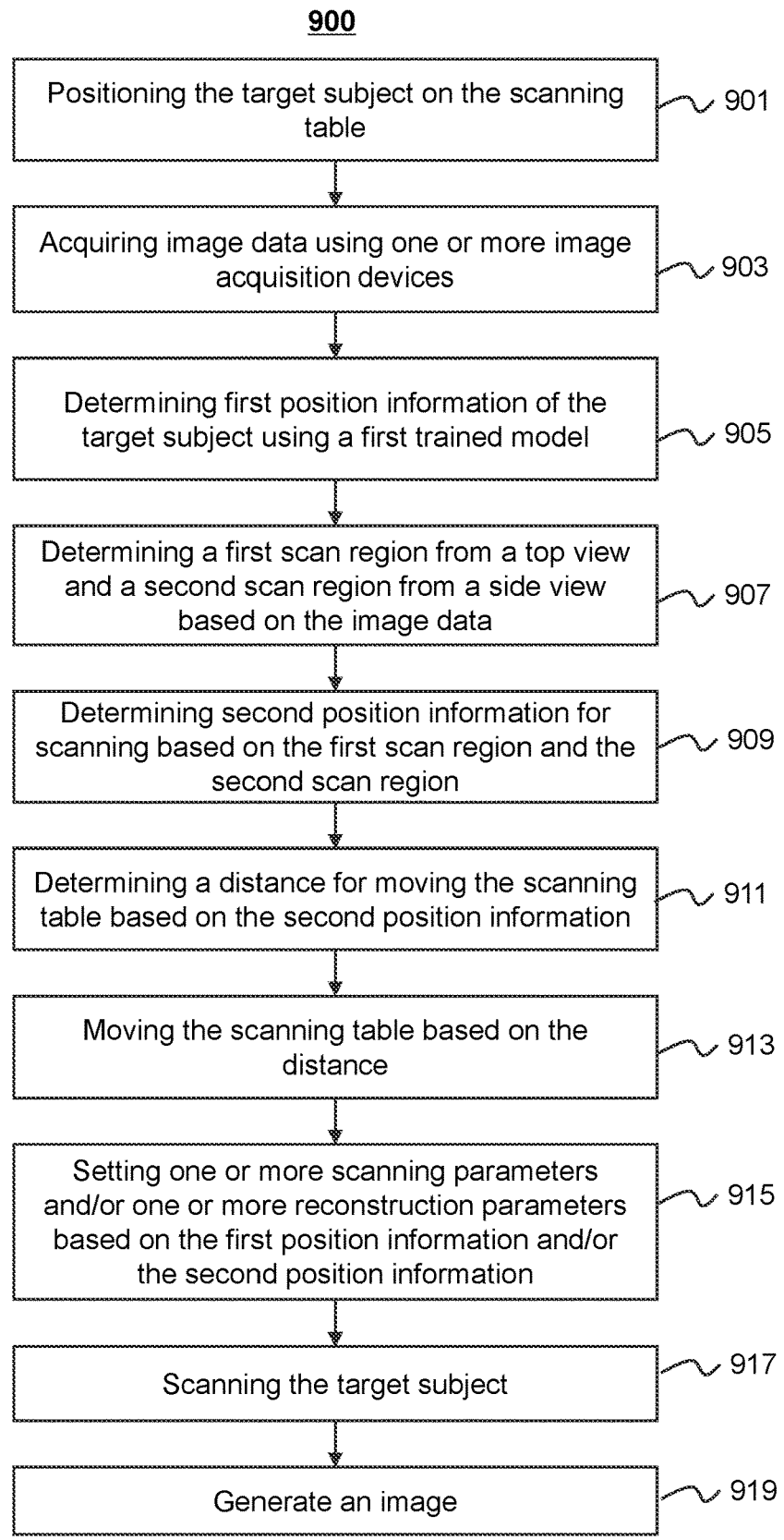
FIG. 9 is a flowchart illustrating an exemplary process for scanning a target subject according to some embodiments of the present disclosure.

FIG. 9 is a flowchart illustrating an exemplary process 900 for scanning a target subject according to some embodiments of the present disclosure.

In 901, the target subject may be positioned on the scanning table 114. The target subject may be positioned automatically or under a guidance of an operator (e.g., a doctor, a radiographer, etc.). The target subject may be positioned according to the eight kinds of first positions mentioned in the present disclosure.

In 903, image data of the target subject may be acquired using one or more image acquisition devices 160. For example, a camera placed over the scanning table 114 at a first distance from the scanning table 114 may acquire image data from a top view of the target subject. As another example, a camera placed in a horizontal direction of the scanning table 114 at a second distance from the scanning table 114 may acquire image data from a side view of the target subject.

In 905, first position information of the target subject may be determined using a first trained model. In some embodiments, the first trained model may be trained using one or more deep learning techniques. The first position information may be determined as described in 703.

In 907, a first scan region from a top view and a second scan region from a side view of the target subject may be determined based on the image data acquired in 903. The combination of the first scan region and the second scan region may locate a portion in a three-dimensional space of the target subject to be scanned. For example, if the target subject's stomach is to be scanned, a three-dimensional region of the stomach may correspond to a two-dimensional scan region in a coronal section (e.g., the first scan region) and a two-dimensional scan region in a sagittal section (e.g., the second scan region) of the target subject. The first scan region and/or the second scan region may be determined as described in 705. In some embodiments, the first scan region and/or the second scan region may be determined using a deep learning model, as described elsewhere in the present disclosure. Using the deep learning model, one or more portions of the image data that correspond to the first scan region and/or the second scan region may be identified.

In 909, second position information for scanning may be determined based on the first scan region and the second scan region determined in 907. In some embodiments, the second position information of the scan region of the target subject may be determined based on marking information in the image data and/or a mapping relation, as described in 705.

In 911, a distance for moving the scanning table 114 may be determined based on the second position information determined in 909. In some embodiments, one or more directions for moving the scanning table 114 may be determined in 911. In some embodiments, the distance and/or direction(s) may be determined based on a comparison of the second position information and a target position, as described in 801.

In 913, the scanning table may be moved based on the distance and/or direction(s) determined in 911. Thus the scan region of the target subject may be placed at a position (e.g., the target position) in the detecting region 113 for scanning, as described in 803.

In 915, one or more scanning parameters and/or one or more reconstruction parameters may be set based on the first position information determined in 905 and/or the second position information determined in 909. The scanning parameter(s) and/or the reconstruction parameter(s) may be set as described in 805.

In 917, the target subject may be scanned based on the scanning parameter(s) set in 915, as described in 807.

In 919, an image may be generated based on the scanning result obtained in 917 and the reconstruction parameter(s) set in 915, as described in 809.

It should be noted that the above description about the process 900 for scanning a target subject is merely provided for the purpose of illustration, and not intended to limit the scope of the present disclosure. For persons having ordinary skills in the art, multiple variations and/or modifications may be made under the teachings of the present disclosure. However, those variations and modifications do not depart from the scope of the present disclosure. For example, 905 may be performed after or simultaneously with 907 through 909. As another example, 915 may be performed before 911. One or more other operations may be added to process 900, or one or more operations may be omitted from process 900. For example, a step for storing the image data acquired in 903 may be added. The stored image data may be further used for training a model.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An imaging method implemented on a computing device having at least one processor and at least one storage device, the method comprising:
   acquiring, by the at least one processor, image data of a target subject positioned on a scanning table of an imaging device;
   determining, by the at least one processor, position information related to a scan region of the target subject by inputting the image data into a machine learning model, the position information including a position of the scan region relative to the scanning table and the imaging device;
   determining, by the at least one processor based on the image data, second position information including a posture of the target subject relative to the imaging device; and
   causing the imaging device to scan the target subject based on the position information and the second position information.

2. The method of claim 1, wherein
   the image data of the target subject comprises a first image of the target subject and a second image of the target subject,
   the first image of the target subject corresponds to a top view of the target subject, and
   the second image of the target subject corresponds to a side view of the target subject.

3. The method of claim 2, wherein the determining the position information related to the scan region of the target subject comprises locating the scan region in at least one of the first image or the second image.

4. The method of claim 1, wherein the determining, by the at least one processor based on the image data, second position information comprises:
   determining the second position information by inputting the image data into a second machine learning model.

5. The method of claim 4, wherein the second machine learning model is trained using a plurality of groups of training images of at least one sample subject, each group of training images corresponding to a classification of posture.

6. The method of claim 1, wherein the causing the imaging device to scan the target subject based on the position information and the second position information comprises:
   determining a distance for moving the scanning table based on the position information; and
   causing the scanning table to be moved by the distance.

7. The method of claim 6, wherein the causing the imaging device to scan the target subject based on the position information and the second position information further comprises:
   determining at least one scanning parameter based on the second position information; and
   causing the imaging device to scan the target subject based on the at least one scanning parameter.

8. The method of claim 7, wherein the causing the imaging device to scan the target subject based on the position information and the second position information further comprises:
   setting a reconstruction parameter based on the position information and the second position information of the target subject.

9. The method of claim 8, further comprising:
   generating an image based on the scanning result and the reconstruction parameter.

10. The method of claim 9, wherein the generated image meets a standard of the digital imaging and communications in medicine (DICOM).

11. The method of claim 7, wherein the at least one scanning parameter includes at least one of a tube voltage, a tube current, a scanning time, a field of view, a matrix, a collimation, an acquisition channel, a slice thickness, a slice gap, a pitch, a rotation speed, or a cardiac gating.

12. The method of claim 1, wherein the second position information of the target subject includes at least one of a head first-prone position, a head first-supine position, a head first-decubitus right position, a head first-decubitus left position, a feet first-decubitus right position, a feet first-decubitus left position, a feet first-prone position, or a feet first-supine position.

13. The method of claim 1, wherein the determining the position information related to a scan region of the target subject by inputting the image data into a machine learning model comprises:
   determining a portion of the image data that corresponds to the scan region of the target subject; and
   determining the position information of the scan region based on the portion of the image data using the machine learning model.

14. The method of claim 13, wherein the machine learning model is trained using a plurality of training images corresponding to a plurality of sample scan regions of at least one sample subject.

15. The method of claim 13, wherein the determining the portion of the image data that corresponds to the scan region of the target subject comprises:
   determining a first candidate scan region based on a first image corresponding to a top view of the target subject; and
   determining a second candidate scan region based on a second image corresponding to a side view of the target subject; and
   determining the portion of the image data that corresponds to the scan region of the target subject based on the first candidate scan region and the second candidate scan region.

16. The method of claim 13, wherein the determining the position information of the scan region comprises:
   determining a mapping relation between the portion of the image data and location information related to the imaging device; and
   determining the position information based on the mapping relation.

17. The method of claim 1, the imaging device comprises a computed tomography scanner.

18. An imaging system, comprising:
at least one processor, and
a storage device configured to store a set of instructions, wherein when the set of instructions is executed by the at least one processor, the system is caused to effectuate a method comprising:
acquiring image data of a target subject positioned on a scanning table of an imaging device;
determining position information related to a scan region of the target subject by inputting the image data into a machine learning model, the position information including a position of the scan region relative to the scanning table;
determining, based on the image data, second position information including a posture of the target subject relative to the imaging device; and
causing the target subject to be scanned by the imaging device based on the position information and the second position information.

19. The system of claim 18, wherein determining second position information based on the image data comprises:
determining the second position information by inputting the image data into a second machine learning model.

20. A non-transitory computer-readable medium including executable instructions that, when executed by at least one processor, cause the at least one processor to effectuate a method comprising:
acquiring image data of a target subject positioned on a scanning table of an imaging device;
determining, based on the image data, second position information including a posture of the target subject relative to the imaging device;
determining position information related to a scan region of the target subject by inputting the image data into a machine learning model, the position information including a position of the scan region relative to the scanning table and the imaging device; and
causing the target subject to be scanned by the imaging device based on the position information and the second position information.

\* \* \* \* \*